US007645591B2

(12) United States Patent
Lilius et al.

(10) Patent No.: US 7,645,591 B2
(45) Date of Patent: Jan. 12, 2010

(54) METHOD FOR DETERMINING THE NATURE OF AN INFECTION

(75) Inventors: Esa-Matti Lilius, Vaakunatie 10 as. 9, Fin-20780 Kaarina (FI); Jari Nuutila, Betaniankatu 19 as. 8, Fin-20810 Turku (FI)

(73) Assignees: Esa-Matti Lilius, Kaarina (FI); Jari Nuutila, Turku (FI)

( * ) Notice: Subject to any disclaimer, the term of this patent is extended or adjusted under 35 U.S.C. 154(b) by 987 days.

(21) Appl. No.: 10/479,656

(22) PCT Filed: Jun. 3, 2002

(86) PCT No.: PCT/FI02/00472

§ 371 (c)(1),
(2), (4) Date: Jan. 14, 2004

(87) PCT Pub. No.: WO02/099433

PCT Pub. Date: Dec. 12, 2002

(65) Prior Publication Data

US 2004/0171013 A1     Sep. 2, 2004

(30) Foreign Application Priority Data

Jun. 4, 2001    (FI) ................................. 20011168

(51) Int. Cl.
*G01N 33/554* (2006.01)
*G01N 33/53* (2006.01)
*A61K 39/38* (2006.01)

(52) U.S. Cl. ..................... 435/7.32; 435/7.1; 424/184.1

(58) Field of Classification Search ................... 435/7.1
See application file for complete search history.

(56) References Cited

U.S. PATENT DOCUMENTS 5,108,899 A * 4/1992 Allen ......................... 435/7.21
5,804,370 A * 9/1998 Romaschin et al. ............. 435/5

FOREIGN PATENT DOCUMENTS

| WO | WO-94/29728 | 12/1994 |
| WO | WO 9429728 A1 | 12/1994 |
| WO | WO-95/29404 | 11/1995 |
| WO | WO 9529404 A1 | 11/1995 |
| WO | WO-96/32645 | 10/1996 |
| WO | WO 9632645 A1 | 10/1996 |
| WO | WO-00/55359 | 9/2000 |
| WO | WO 0055359 A1 | 9/2000 |

OTHER PUBLICATIONS

Lindena et al (Mechanisms of non-opsonized zymsan and luminal enhanced chemiluminescence in whole blood and isolated phagocytes, J. Clin. Chem. Biochem, 1987; 25: 765-778).*
Leino et al (Febrile infection chanbes the expression of IgG Fc receptors and complement receptors in human neutrophils in vivo, Clin. Exp. Immunol, 1997; 107: 37-43).*
McCafferty et al (The influence of age and sex on phagocytic chemiluminescence, Journal of bioluminescence and chemiluminescence, 1995; 10(1): 41-8).*
Gronlund et al (Mode of delivery directs the phagocyte functions of infants for the first 6 months of life, Clin. Exp. Immunol, 1999; 116: 521-526).*
Dorlands Medical Dictionary- anticoagulant (www.mercksource.com).*
Witko-Sarsat, et al., "Priming of Blood Neutrophils in Children with Cystic Fibrosis: Correlation Between Functional and Phenotypic Expression of Opsonin Receptors Before and After Platelet-Activating Factor Priming", The Journal of Infectious Diseases Society of America, pp. 151-162, 1999.
Gronlund, et al., "Mode of Delivery Directs the Phagocyte Functions of Infants for the First 6 Months of Life", Clinical and Experimental Immunology, pp. 521-526, 1999.
Leino, et al., "Febrine Infection Charges the Expression of IgG Fc Receptors and Complement Receptors in Human Neutrophils in vivo", Clinical and Experimental Immunology, pp. 37-43, 1997.
Witko-Sarsat et al., *Journal of Infectious Diseases*, vol. 179, No. 1, (1999), pp. 151-162, Medline AN 1999059863.
Leino et al., *Clinical and Experimental Immunology*, vol. 107, No. 1, (1997), pp. 37-43, Biosis PREV199799379713.
Isolauri et al., *Journal of Allergy and Clinical Immunology*, vol. 99, No. 5, (1997), pp. 707-713, Biosis PREV199799589021.
Grönlund et al., *Clinical and Experimental Immunology*, vol. 116, No. 3, (1999), pp. 521-626, Medline AN 1999291019.

* cited by examiner

*Primary Examiner*—Robert B Modesi
*Assistant Examiner*—Lakia J Tongue
(74) *Attorney, Agent, or Firm*—Birch, Stewart, Kolasch & Birch, LLP

(57) ABSTRACT

The present invention relates to differential diagnostics, and provides a method for determining if an infection detected in a patient is of bacterial or of viral origin. In the method chemiluminescence of phagocytic cells induced by non-opsonized zymosan in a blood sample is measured and the expression of Complement Receptor 1 (cr1) is determined. The value when multiplying chemiluminescence with the CR1 expression is compared with method-specific average values for bacterial and viral infections. The invention also provides test kits for accomplishing the method of the invention.

8 Claims, 7 Drawing Sheets

METHOD FOR DETERMINING THE NATURE OF AN INFECTION

CROSS-REFERENCE TO RELATED APPLICATIONS

The present application is a national stage entry of International Application No. PCT/FI02/00472, filed Jun. 3, 2002.

FIELD OF THE INVENTION

The present invention relates to differential diagnostics, and provides a simple and rapid method for determining if an infection detected in a patient is of bacterial or of viral origin. The invention also provides diagnostic test kits for accomplishing the method of the invention.

BACKGROUND OF THE INVENTION

A microbial infection in an organism launches the organism's own, complicated defence mechanisms against the infection. Laboratory tests and clinical investigation of a patient reveal typical changes. Infections, but also traumas, inflammatory processes and cancers cause in an organism changes, which are called acute phase reactions. These changes are called acute, since they appear within a few hours or days from the infection or trauma. The background of the changes lies in the increase of the protein synthesis in liver caused by interleukin 1 and interleukin 6 which are formed as a consequence of the infection or inflammation.

Such proteins of the acute phase include baptoglobin, ceruloplasmin, fibrinogen, amyloid-A and C-reactive protein (CRP). It is most useful to determine CRP in blood, since its concentration increases in connection with an infection, inflammation and tissue damage. The changes in the serum concentration of CRP can increase up to hundredfold. It is also fairly cheap to determine CRP in serum, wherefore CRP has proved a convenient diagnostic tool. The main applications of CRP are detection of infectious diseases and differential diagnostics between bacterial and viral infections. However, in addition to serious bacterial infections, a CRP value can be very high also in invasive viral infections, as e.g. epidemic nephropathy and herpes virus infections of mouth and throat. The concentration of CRP illustrates mainly the invasive character of the infection as well as related tissue damage and the action of inflammatory cells. Consequently, CRP is not as such specific in regard to the source of the infection.

In clinical work CRP is today the most important acute phase protein, because it changes quickly and is suitable for monitoring the inflammatory level of various diseases, and thus also the effect of treatment. CRP concentration can change substantially to either direction even in less than 24 hours. Instead, another commonly used measure of inflammation, Erythrocyte Sedimentation Rate (ESR), changes much slower. It does not increase substantially until one week after the initiation of the inflammation and, correspondingly, its half-time is weeks. In differential diagnostics of infectious diseases ESR alone has no specific value.

In practical clinical work it would be very important to have also other than microbiological means to assess a possible viral or bacterial infection as a cause of the deterioration of the clinical state of a patient. Consequently, a reliable and rapid detection of an infection, or the nature of the infectious agent is important to enable a correct diagnosis. The appropriate treatment of the infection can be stared as soon as possible, or a proper assessment can be made if anti-inflammatory treatment is necessary at all. A prolonged hospitalising and intravenous antibiotic treatment can thus be avoided.

It is known that different diseases cause changes in the amounts of the leukocyte surface receptors. Such receptors have been studied for instance in atopic and cancer patients. Leino et al. (1997) and Isolauri el al. (1997) have studied the receptor changes in febrile and atopic patients, respectively. However, the knowledge of the receptor changes in such conditions has not been applied to differential diagnostics, nor has such a knowledge been combined with ESR data or the data of chemiluminescence response of whole blood, ie. the level of cell activation, as has been done in the present invention.

SUMMARY OF THE INVENTION

We have now developed a method which enables rapid detection of the source of an infection in a patient, i.e. a rapid method for determining if an infection detected is of bacterial or of viral origin.

The method according to the present invention is based on the analysis of the surface receptors of phagocytic cells, as well as the level of cell activation. The method is carried out by determining the expression of the Complement Receptor 1 (CR1) of the phagocytic cells of peripheral blood. In addition, the chemiluminescence response of whole blood against non-opsonized zymosan (NWBCL) is determined. In a preferred embodiment of the invention the Erythrocyte Sedimentation Rate (ESR) of the blood sample is determined as well.

Consequently, based on the above-indicated measurements we have developed three equations, which can be used in calculating relevant values for diagnosis. The values obtained are subsequently compared with method-specific average values for bacterial and viral infections and, when appropriate, with method-specific control values.

A primary object of the present invention is thus a method for distinguishing a bacterial infection from a viral infection in a patient. A further object of the invention is a diagnostic test kit for accomplishing the method.

In the following the preferred embodiments of the invention are described with reference to the enclosed Drawings.

DETAILED DESCRIPTION OF THE INVENTION

Figure 1:
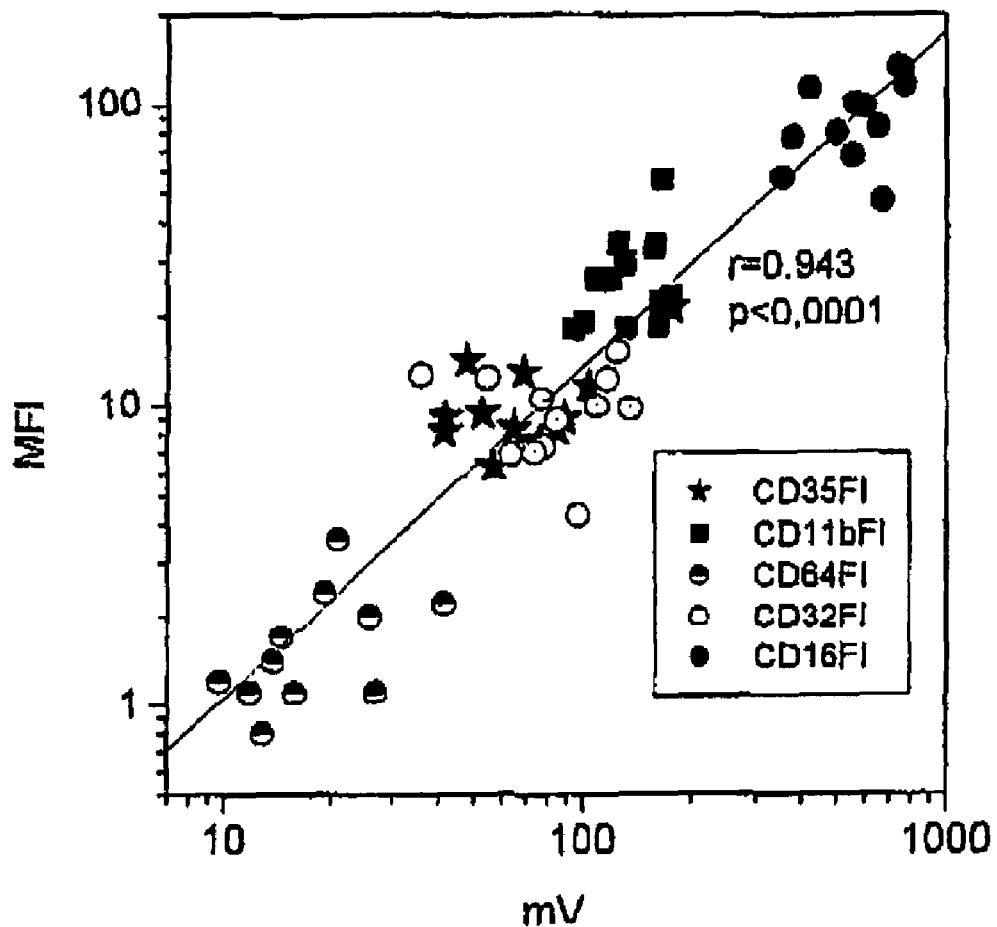
FIG. 1 Comparison of flow cytometric (mean fluorescent intensity, MFI) and lumino-metric (mV) measurements of various receptor expressions (CD35=CR1; CD11b=CR3; CD64=FcγRI; CD32=FcγRII; CD16=FcγRIII).

Abbreviations
CL chemiluminescence
CR1 complement receptor 1
CRP C-reactive protein
ESR Erythrocyte Sedimentation Rate
FcγR receptor for binding the Fc region of antibodies. Leukocytes have three types of Fcγreceptors: I (FcγRI), II (FγRII) and III (FγyRIII)
$Fc\gamma RI_M / Fc\gamma RII_N$ expression in monocytes divided with FcγRII expression in neutrophils
gHBSS-buffer Hank's balanced salt solution supplemented with 0.1% gelatine
HBSS-buffer Hank's balanced salt solution
MFI mean fluorescence intensity
$(M/N)_{CR1}$ CR1 expression in monocytes divided with CR1 expression in neutrophils
mV millivolts
NOZ non-opsonized zymosan
NWBCL chemiluminescence response of whole blood against non-opsonized zymosan [expressed per blood volume (µl)]
RT room temperature
WB whole blood The method used in this invention is based on the fact that different diseases cause changes in the amounts of the leukocyte surface receptors, and that they increase the activation level of the cells. It depends on the cause of the infection, which one(s) of the various leukocyte defense mechanisms is/are activated, and how broadly the activation occurs. In the activation of phagocytic cells the expression of certain receptors on the surface of the cells increases, and this phenomenon can be nurtured using specific labelled antibodies. The receptors to be examined are commonly known receptors of neutrophis or monocytes involved in phagocytosis and complement function.

The receptor assays according to the method of this invention are carried out e.g. using an immunoreaction with an antibody specific to each receptor using flow cytometric analysis.

The method according to the invention is in general carried out by separating phagocytic cells from a blood sample drawn from a patient having an infection, and measuring the expression of leukocyte surface receptors of said cells. The blood sample is taken into a test tube containing an anticoagulant. The phagocytic cells can then be separated by osmotic lysis of erythrocytes of the blood sample, by adding e.g. NH$_4$Cl and washing the debris of the lysed erythrocytes and plasma out of the blood sample, whereby only leukocytes will be left.

To measure the receptor expression the leukocytes are labelled in cold environment (at about +4° C.) with a fluorescence-labelled monoclonal antibody specific to the receptor in question. The mean fluorescence intensity (MFI) of each cell type (neutrophils and monocytes) is obtained by flow cytometry. From the results the amount of each cell type is obtained, one pulse corresponding to one cell, and the amount of the receptor to be measured, as well as the percentage of the cells in which the receptor is present.

However, the receptor assays can also be earned out luminometrically. Flow cytometric receptor expression studies are relatively expensive, whereas luminometric assays are fairly cheap and rapid. At best a luminometric assay can be effected of finger tip blood using a luminometer, the use of which does not demand noticeable laboratory expertise.

When the receptor expression measurement are carried out luminometrically, the leukocytes are labeled with the same monoclonal antibodies as in flow cytometry, but now luminescence-labelled, whereby the amount of receptors is obtained luminometrically as the magnitude on the A luminometric receptor expression assay is preferably carried out as follows: The leukocytes are fist labelled with a primary monoclonal antibody specific to the receptor to be measured. The mixture obtained is washed with a suitable buffer and then it is incubated with a secondary antibody attached to an enzyme conjugate. A substrate to the enzyme conjugate is added into the mixture, and the luminometric intensity is measured. All cells to which the antibody is attached give a light signal.

A preferable enzyme conjugate for the present luminometric assay is alkaline phosphatase, which is easy to use, and for which a stable substrate solution is available. In addition, to decrease the mV-response of the cell background the alkaline phosphatase of the leukocytes can be eliminated with a blocker.

In a preferred embodiment of the invention the method is effected as follows:

A blood sample is collected from a patient into a test tube containing an anticoagulant. For instance, heparin or EDTA can be used as anticoagulants. Heparin is preferred for the purposes of the present invention, since in our experiments the differentiation was found to be more distinct when using heparin than when using EDTA as anticoagulant.

Subsequently, the activation level of phagocytic cells is determined by measuring the phagocytosis of zymosan in whole blood. An aliquot of the whole blood sample obtained is thus subjected to the NWBCL assay as defined above, by adding into said blood sample non-opsonized zymosan and luminol in a suitable buffer. Zymosan induces chemiluminescence of the phagocytic cells present in the sample, and said chemiluminescence is measured by luminometer. It is preferable to use zymosan, which has been sonicated during its preparation.

Red blood cells are lysed and washed out, and the expression of the Complement Receptor 1 (CR1) in the remaining leukocytes is determined. If the expression is measured by flow-cytometry, a Mean Fluorescence Intensity (MFI) value is obtained, showing the average amount of the receptor on the cell, separately for each cell type (neutrophils and monocytes). If the expression is measured by luminometry, a luminiscence signal in millivolts (mV) is obtained. However, it should be noted that Mean Fluoresceace Intensity is not an absolute measure of the receptor amount, but it gives a relative value, which depends on the antibody aliquot used, and also on the equipment used. The same applies to the mV values obtained by lumiometry.

Figures 4A, 4B:
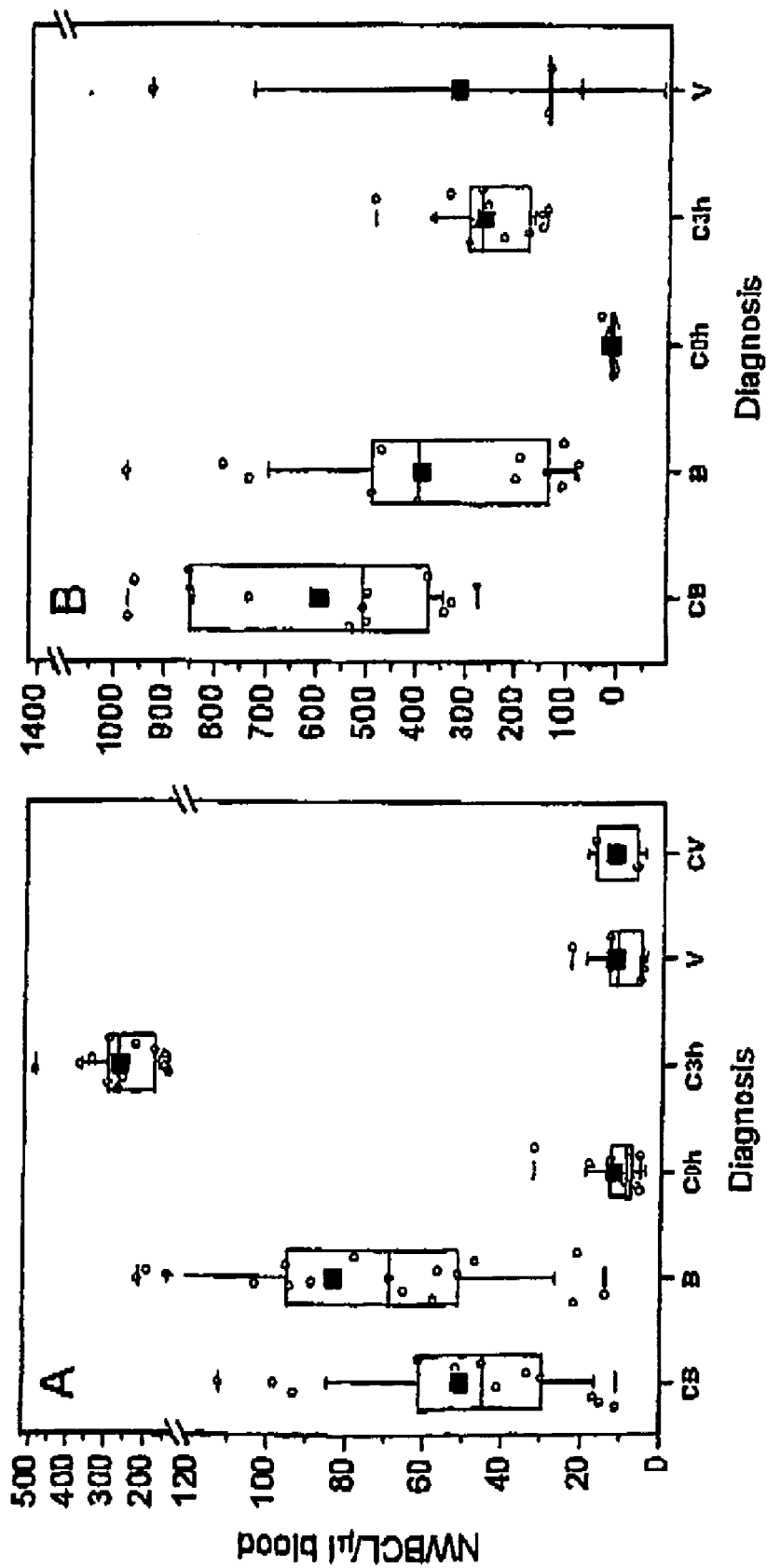
FIGS. 4A and 4B Luminol-amplified chemiluminescence of whole blood; NWBCL/µl blood. 4A: Experiment I; 4B: Experiment II. Patient groups as in FIG. 2.

The appended FIGS. 2 (2A, 2B) and 3 (3A, 3B) show the receptor expression values of neutrophils and monocytes, respectively, as measured by flow cytometry. On the other hand, FIG. 1 shows that the results obtained flow cytometrically and luminometrically are comparable with each other. Furthermore, FIGS. 4A and 4B show the results of the NWBCL measurements.

Figures 5A, 5B:
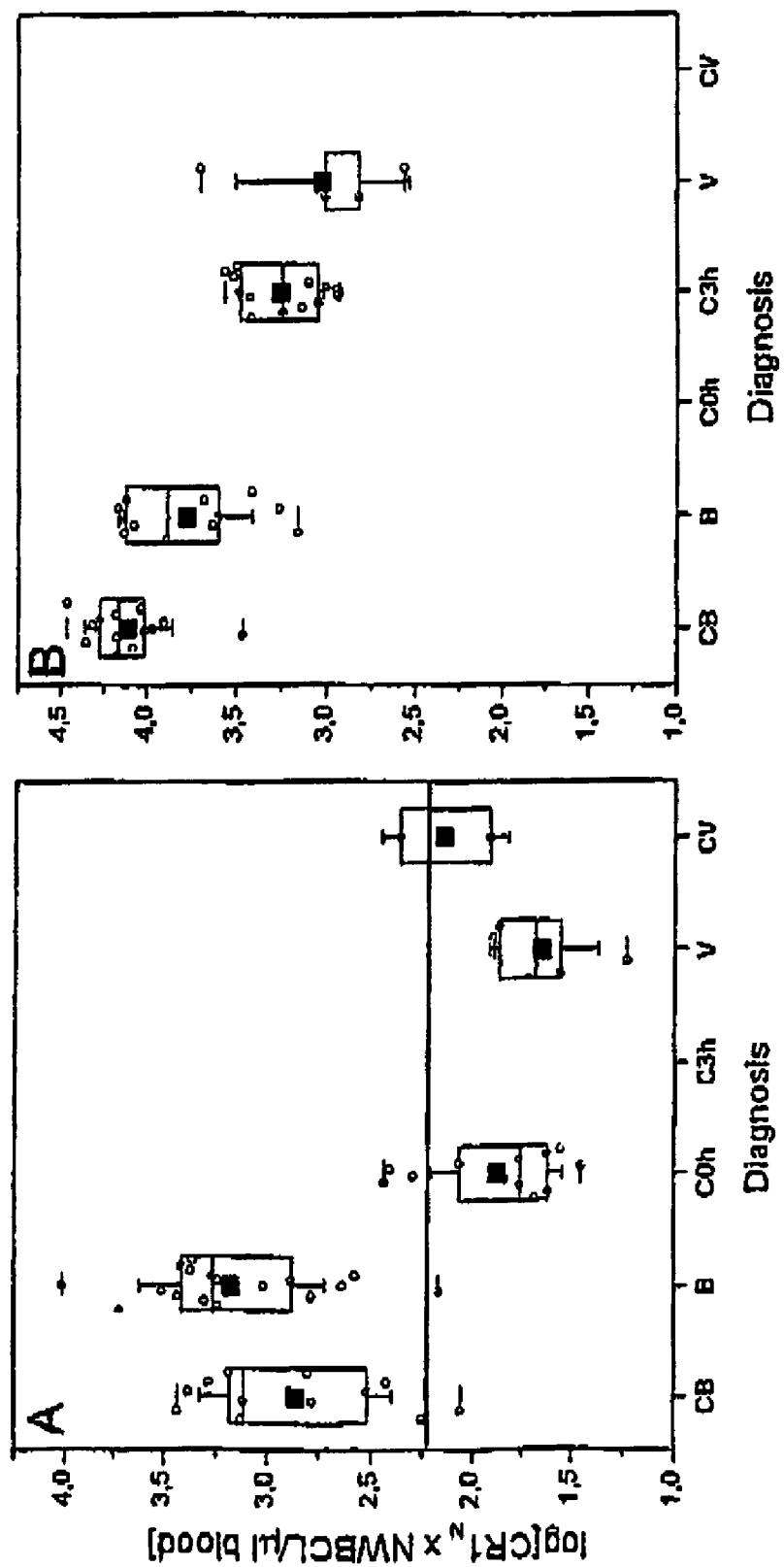
FIGS. 5A and 5B show the results obtained using Equation #1, CR1×NWBCL/µl blood, 5A: Experiment I, 5B: Experiment II. Patient groups as in FIG. 2.

After obtaining the values as indicated above, the calculations for diagnosis are made by Equation #1: CR1×NWBCL/µl blood (FIGS. 5A and 5B). The resultant value is then compared to method-specific average values for bacterial and viral infections.

In a still more preferred embodiment of the invention, the Erythrocyte Sedimentation Rate (ESR) in the blood sample is also measured, and the resultant value calculated from the above Equation #1 is multiplied with said ESR, so obtaining Equation #2: CR1×NWBCL/µl blood×ESR FIGS. 6A and 6B). Using this equation a value is obtained, which shows a very distinct differentiation in diagnosis.

Figure 7B:
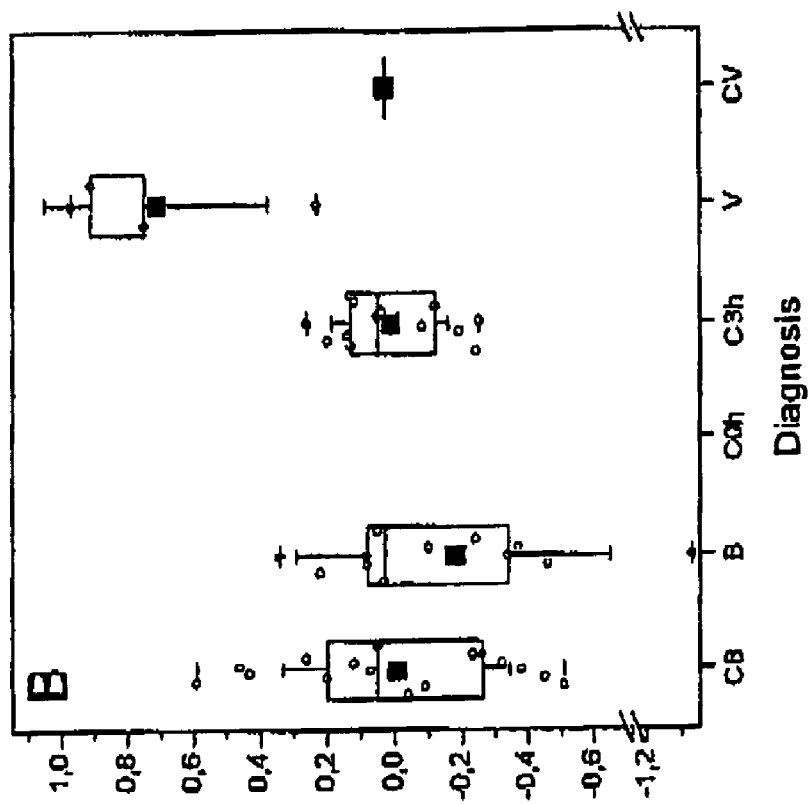
FIGS. 7A and 7B show the results obtained using Equation #3, $(M/N)_{CR1} \times (Fc\gamma RI_M / Fc\gamma RII_N)$, 7A: Experiment I, 7B: Experiment II. Patient groups as in FIG. 2.
Figure 7A:
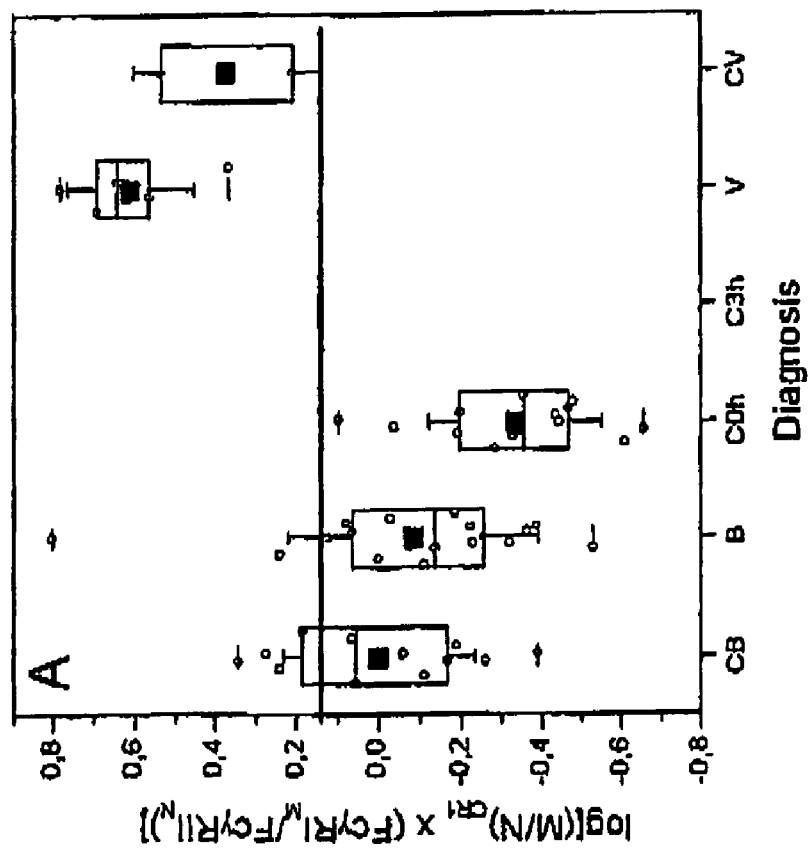

In case the result obtained by Equation #1 or #2 is unclear, it may be confirmed by a third method, which is effected as follows. The expression of the Complement Receptor 1 (CR1) is determined by flow cytometry both in monocytes and in neutrophils. In addition, the expression of the FcγRI receptor is determined in monocytes, and the expression of FcγRI receptor in neutrophils. The resultant value for diagnosis is calculated from Equation #3: $(M/N)_{CR1}=(Fc\gamma RI_M/Fc\gamma RII_N)$, wherein M is the receptor expression in monocytes and N is the receptor expression in neutrophils (FIGS. 7A and 7B).

It should be noted that Equation #3 cannot be used when the receptor expressions are measured by luminometry. This is due to the fact that while measuring chemiluminescence, all of the phagocytic cells are in the same population, and thus the signals of neutrophils and monocytes cannot be distinguished. Consequently, by a luminometric method the receptor expression level of the whole leukocyte population is obtained whereas flow cytometry gives information of the individual receptor expressions of neutrophils and monocytes.

It should also be noted that the numerical values obtained from the above equations vary depending on the labelling procedure, i.e, how the antibodies have been labelled, or how successful the labelling was. Consequently, it is not possible to give any specific cut-off values, above which a patient may have e.g. a bacterial infection, but the values obtained are always method-specific. For instance, when building up the procedures, the antibodies to be used should be selected, and the same antibodies should be used consistently thereafter. When changing the antibody lot, the new lot (the intensity thereof) should be proportioned to the previous one. Furthermore, as appreciated by a man skilled in the art, it is advisable to run control samples first, in order to define the basic level of the numerical values obtained from the equations. It is also advisable to determine method-specific control values regularly. Such calibration and certifying measures are within the expertise of a man skilled in the art.

Furthermore, it is preferable to carry out the determinations as soon as possible after collecting a blood sample, and preferably within two hours, more preferably within one hour from drawing the sample. It was found in our experiments that the differentiation was less distinct in samples older than two hours. The appended FIGS. 5A, 6A and 7A reveal the results of Experiment I, wherein the time lag between sampling and the assays was 1 to 2 hours, and the appended FIGS. 5B, 6B and 7B reveal the results of Experiment II, wherein said time lag was 2 to 3 hours. Consequently, when comparisons with control values are made, in Experiment I comparisons should be made to the 0 hour controls (C0h), and in Experiment II to the 3 hour controls (C3h).

The present invention relates further to diagnostic test kits for carrying out the method according to the invention, the test kits comprising (1) means for determining the expression of the receptors either by flow cytometry or luminometry, (2) means for luminometric determination of the phagocytic activity of the cells, and (3) written directions, including Equations #1 and #2, for calculating the resultant value for diagnosis.

For an assay where the receptor expressions are determined by flow cytometry, a test kit comprises (1) antibodies specific to the receptors to be determined, a fluorecence label, and buffers necessary in the assay, (2) luminol and non-opsonized zymosan, and (3) written directions, including Equations #1 and #2, for calculating the resultant value for diagnosis.

For an assay where the receptor expressions are determined by luminometry, a test kit comprises (1) primary antibodies specific to the receptor to be determined, secondary antibodies with an enzyme conjugate, a substrate to the enzyme conjugate, and buffers necessary in the assay, (2) luminol and non-opsonized zymosan, and (3) written directions, including Equations #1 and #2, for calculating the resultant value for diagnosis.

For the confirmative assay, resulting to Equation #3, a test kit comprises (1) antibodies specific to the receptors to be determined, a fluorescence label, buffers necessary in the assay, and (2) written directions, including Equation #3, for calculating the resultant value for diagnosis.

Experimental

Study Subjects and Measurements

The inflammation samples (n=71, 10 ml of heparin-anticoagulated blood) were taken from hospitalized adults on admittance at the Turku University Hospital. The subjects were divided into groups on the basis of their diagnosis. The abbreviations for different subject groups are the following: B: confirmed bacterial infection; CB: clinical bacterial infection; V: confirmed viral infection; CV: clinical viral infection (see FIG. 2 (2A and 2B) for explanation of the terms). The receptor expressions of neutrophils and monocytes, the Erythrocyte Sedimentation Rate, and the chemiluminescence response of whole blood against non-opsonized zymosan (NWBCL) were determined.

Patient Subgroups and Controls

The samples were analysed in two terms: Experiment I (n=38) (the samples were collected between December 1998 and April 1999), and Experiment II (n=33) (the samples were collected between September 1999 and May 2000). The time lag between the sampling and the analysis was 1-2 hours in Experiment I and 2-3 hours in Experiment II, due to the daily routines at the hospital. The influence of the increased time lag on receptor expression and CL-response of phagocytes was investigated. The results of Experiment I were compared with a baseline group (n=13) and those of Experiment 11 with a 180-min group (n=13). Furthermore, in Experiment II and the 180-min controls the CL measurements were done using unsonicated zymosan to explore the effect of particle size on the chemiluminescence responses. The abbreviations for the two control groups are C0h: baseline control samples after 0 hour preservation; C3h: 180-min control samples after 3 hour preservation.

Materials and Methods Used

Collection and Preparation of Blood Samples

Venous blood samples were collected from the study subjects into test tubes with heparin. 1 ml of the anticoagulated blood was mixed with 10 ml of 0.83% $NH_4Cl$ including 370 mg/l disodium EDTA. The suspension was kept at room temperature (RT) for 15 minutes, after which leukocytes were centrifuged for 10 minutes at 400×g. The leukocytes were resuspended to 1 ml of gHBSS buffer.

Erythrocyte Sedimentation Rate (ESR) was measured in a conventional manner.

Preparation of non-opsonized zymosan (NOZ)

Zymosan A, (Sigma Chemical Co., St. Louis, Mo., USA) a cell wall preparation from *Saccharomyces cerevisiae*, was used as the phagocytosable particle in the luminometric respiratory burst studies. Zymosan A (20 mg/ml HBSS-buffer) was heated in a boiling water bath for 20 min and disintegrated by powerful sonication, for 20 seconds with 11 microns peak-to-peak amplitude, washed twice with HBSS buffer. The stock solution (20 mg of NOZ/ml in HBSS buffer) was used for the luminometric experiments.

Measurement of Luminol-amplified Chemiluminescence

In the zymosan-induced whole blood chemiluminescence measurements (NWBCL), the reaction mixture contained a total volume of 0.5 ml of gHBSS including 0.4 mM luminol 1 mg of NOZ and 100 nl of heparin-anticoagulated whole blood (WB). In the control cuvettes, the zymosan was replaced with gHBSS. First the buffer, luminol, and zymosan were incubated at +37° C. for 30 min to stabilize the reaction temperature, and the isolated leukocytes or whole blood dilution (both kept in RT until used) were added to start the reaction. The reaction was measured in duplicates with a BioOrbit 1251 luminometer with MultiUse 2.01 software (BioOrbit Ltd., Turku, Finland) at +37° C. The CL emission capacity of phagocytes was expressed as the peak value (mV) during the 60 minute period and the time to reach the peak value as the peak time (min). The results are expressed as the peak value as mV/µl whole blood.

Measurement of Receptor Expressions with Flow Cytometer

Measurement of leukocyte receptor expressions was performed using fluorescence (FITC or PE) labelled receptor-specific monoclonal antibodies. The mAbs used were purchased from Immunotech.

Before the measurements of receptor expression, leukocytes ($3 \times 10_5$) were incubated in 50 µl of gHBSS with monoclonal antibodies (0.4 µg) in polystyrene flow cytometer vials for 30 min at +4° C. After incubation, the cells were washed once with cold gHBSS (400×g, 5 min) and resuspended in cold gHBSS. Leukocytes stained with irrelevant mouse immunoglobulins served as controls for correction of leukocyte autofluorescence. A relative measure of receptor expression was obtained by determining the mean fluorescence intensity of 5000 leukocytes by flow cytometer (EPICS XL flow cytometer with an argon ion laser with an 488 nm excitation wavelength (Coulter, Miami, Fla, USA)). Results separately for neutrophils and monocytes were obtained as MFI.

Measurement of Receptor Expressions of Leukocytes with Luminometer

In the luminometic receptor expression assay whole blood ($3 \times 10_5$ leukocytes/50 µl) lysed with $NH_4Cl$ was incubated for 30 min at +4°C. with unlabelled primary receptor-specific monoclonal antibodies (0.4 µg) (Immunotech) produced in mouse. After incubation the excess antibody was washed away with 500 µl of HBSS buffer (0.1% Na-azide)(400×g, 5 min), whereafter the antibodies bound to the receptors were detected by goat-anti-mouse antibody AF-F(ab')$_2$ (Zymed) labelled with secondary alkaline phosphatase (AF). The secondary labelling was effected in a 50 µl volume (HBSS) 30 min +4° C. After incubation the excess AF-labelled secondary antibody was removed by washing the cells three times with 500 µl of HBSS buffer (0.1% Na-azide)(400×g, 5 min). After the washes the cell pellet was suspended quickly into 270 µl of alkaline phosphatase substrate solution (including 42 mg/ml of substrate (AMPPD, Zymed) and a ¹⁄₂₅ dilution of a blocker of endogenic AF (Levamisole, Zymed)). 250 µl of the cell suspension in the substrate solution was transferred into a luminometer cuvette (polystyrene), and chemiluminescence was measured luminometrically. Receptor expression of leukocytes was given as millivolts (mV). Chemiluminescence was measured also from three different background cuvettes:

1. Substrate solution only
2. Cells only
3. Cells +AF-labelled secondary antibody The background cuvettes were handled in the same way as the receptor measuring cuvettes.

Comparison of Flow Cytometric and Luminometric assays

FIG. 1 shows the correlation between the receptor expressions measured by flow cytometer and luminometer. In flow cytometric measurements same primary antibodies were used as in luminometric measurements, but as the secondary antibody a FITC-labelled goat anti-mouse IgG antibody (FITC-F(ab')$_2$, Zymed) was used. In both of the methods the samples were handled in parallel in a similar way, but in the flow cytometric assays the substrate solution was replaced with 500 µl of HBSS buffer, whereafter the flow cytometric assay was performed. FIG. 1 shows that the luminometric assay correlates well with the flow cytometric assay. As the said figure intends to demonstrate the correlation between the two assays, Complement Receptor 3 (CR3) and FcγRIII expressions were determined as well, despite the fact that these receptor expressions are not needed in the equations of the present invention (see legends for FIG. 1).

Results

Receptor Expression of Neutrophils

Figures 2A, 2B:
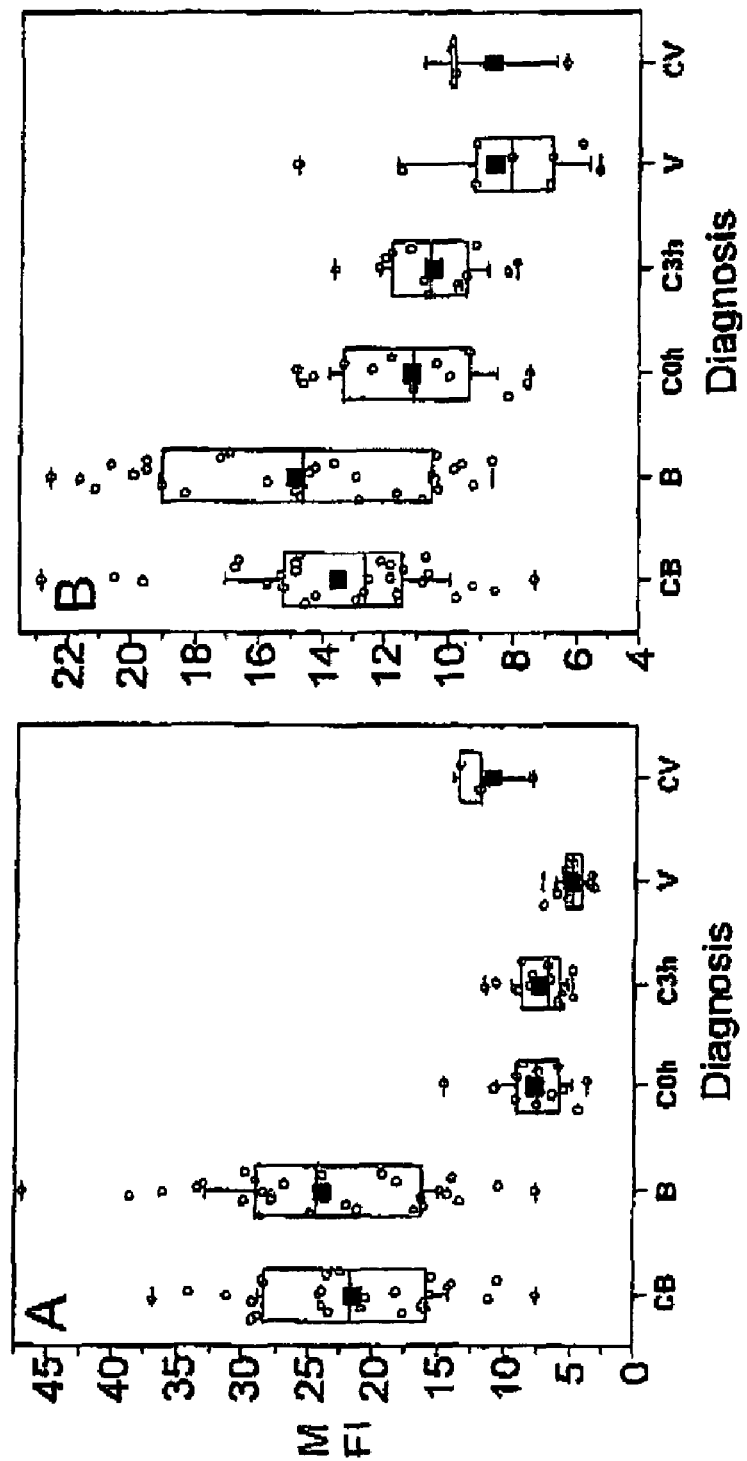
FIGS. 2A and 2B Receptor expressions of neutrophils measured by flow cytometry. (Values from Experiments I and II are taken together. In Experiment I the time lag between sampling and assays was 1 to 2 hours before the determinations, in Experiment II 2 to 3 hours. In addition, in Experiment I sonicated zymosan was used, in Experiment II unsonicated zymosan.) Patient groups (diagnosis): CB=clinical bacterial infection: diagnosis made on the basis of clinical symptoms; B=confirmed bacterial infection: diagnosis confirmed from a blood, urine or tissue sample by microbiological cultivation of bacteria or by serology from serum and/or nasopharyngeal sample; C0h=zero hour control sample (immediate assay); C3h=three hour control sample (sample at room temperature for 3 hours prior to the assay); V=confirmed viral infection: diagnosis confirmed by viral antibody assays; CV=clinical viral infection: diagnosis made on the basis of clinical symptoms. 2A: CR1 (MFI); 2B: FcγRII (MFI). Heparin as anticoagulant.

In confirmed and clinical bacterial infections the expression of CR1 is four-to five-fold compared with confirmed viral infections or controls ($p<0.001$), with viral infections slightly below controls (FIG. 2A). The expression of FcγRII is lower in a viral infection compared with a confirmed bacterial infection and, surprisingly, also with the controls ($p<0.05$)(FIG. 2B).

Receptor Expression of Monocytes

Figures 3A, 3B:
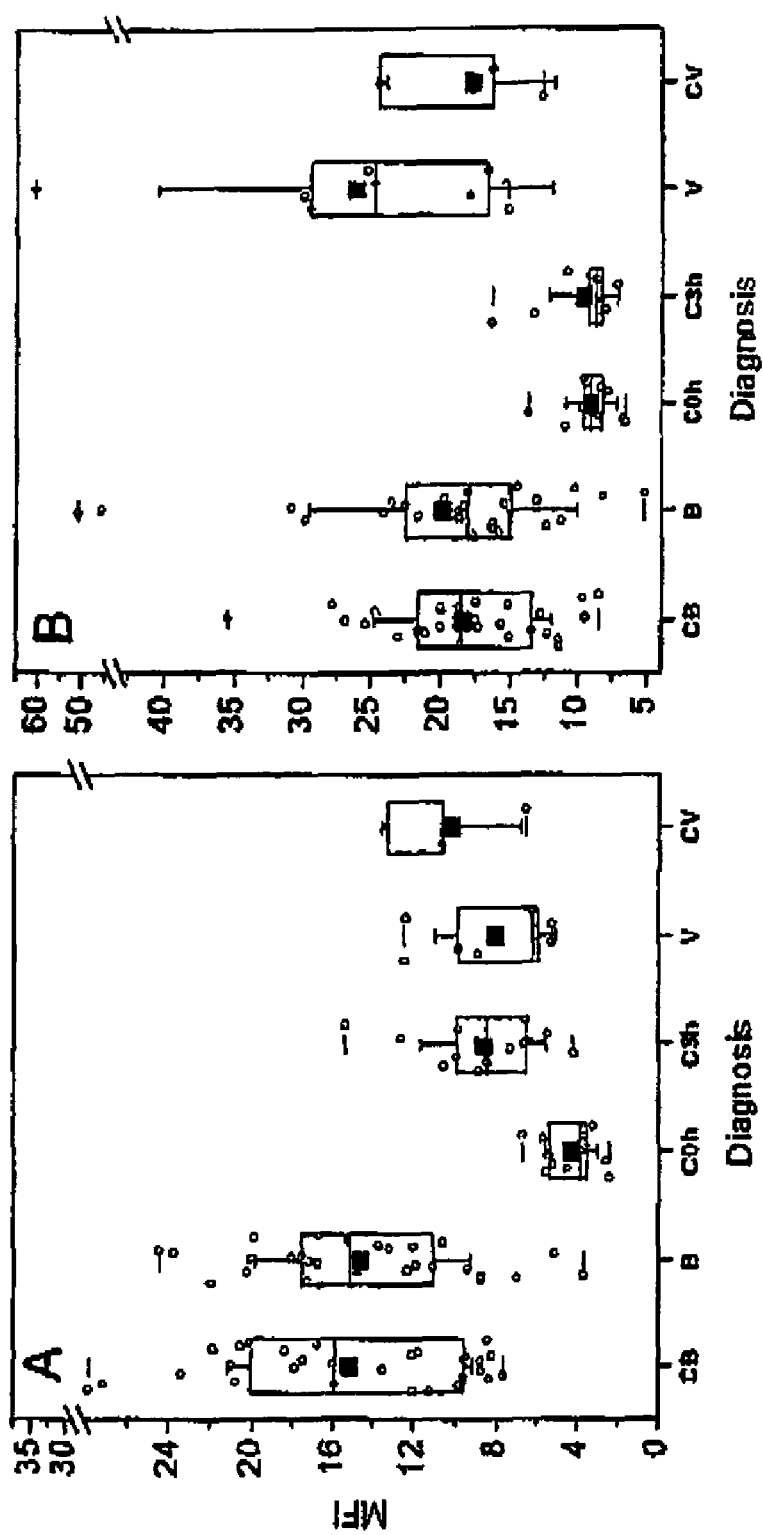
FIGS. 3A and 3B Receptor expressions of monocytes measured by flow cytometry. (Experiments I and II together) 3A: CR1 (MFI); 3B: FcγRI (MFI). Patient groups as in FIG. 2. Heparin as anticoagulant.

As in neutrophils, bacterial infection increases the expression of CR1 in monocytes (FIG. 3A). The increase is four-fold compared with 0 hour control samples ($p<0.001$).and two-fold ($p<0.001$) compared with viral infection or 180-min controls. In a bacterial infection, the expression of CR1 on monocytes is about 65 percent of that of the neutrophils. The expression of monocyte FcγRI was significantly lower in both control groups ($p<0.001$) than in the bacterial and viral infections FIG. 3B). Unlike in neutrophils, there were no differences in the expressions of FcγRI on monocytes between viral and bacterial infections.

Chemiluminescence

The NWBCL-responses of Experiments I and II are presented in FIGS. 4A and 4B, respectively. In Experiment I, the NWBCL response in a confirmed bacterial infection is significantly higher (p<0.001) compared with control (C0h) and a viral infection, whereas in Experiment II, where unsonicated zymosan was used, NWBCL response was not significantly different between controls (C3h) and patients. Thus, it is obvious that the bigger the size of the particles inducing the production of reactive oxygen species (ROS) and the longer the preservation time of the blood sample, the less useful is the NWBCL response in distinguishing a bacterial infection from a viral infection.

Calculations for Diagnosis

Equation #1

Of the measured parameters NWBCL-response, the expression of CR1, and ESR are all strongly increased in a bacterial infection. It is shown in this application that all these parameters can be used in separating bacterial and viral infections. Because the size of zymosan particles and the different preservation time lags of samples had an extensive effect on NWBCL-responses and receptor expressions, the results are expressed separately for Experiment I and Experiment II. The simpliest value, which can be used for sorting can be calculated as CR1×NWBCL (Equation #1), wherein the NWBCL value is expressed per blood volume (µl).

The product of Equation #1 is significantly higher (p<0.001) in bacterial infections compared with viral infections and baseline controls (FIG. 5A). The NWBCL response of 180-min controls, induced by unsonicated zymosan, is equal to the bacterial infections. In spite of significant differences between bacterial infections and viral infections or 180-min controls (p<0.01), the NWBCL response induced by unsonicated zymosan blurs these differences (FIG. 5B).

Equation #2

Figures 6A, 6B:
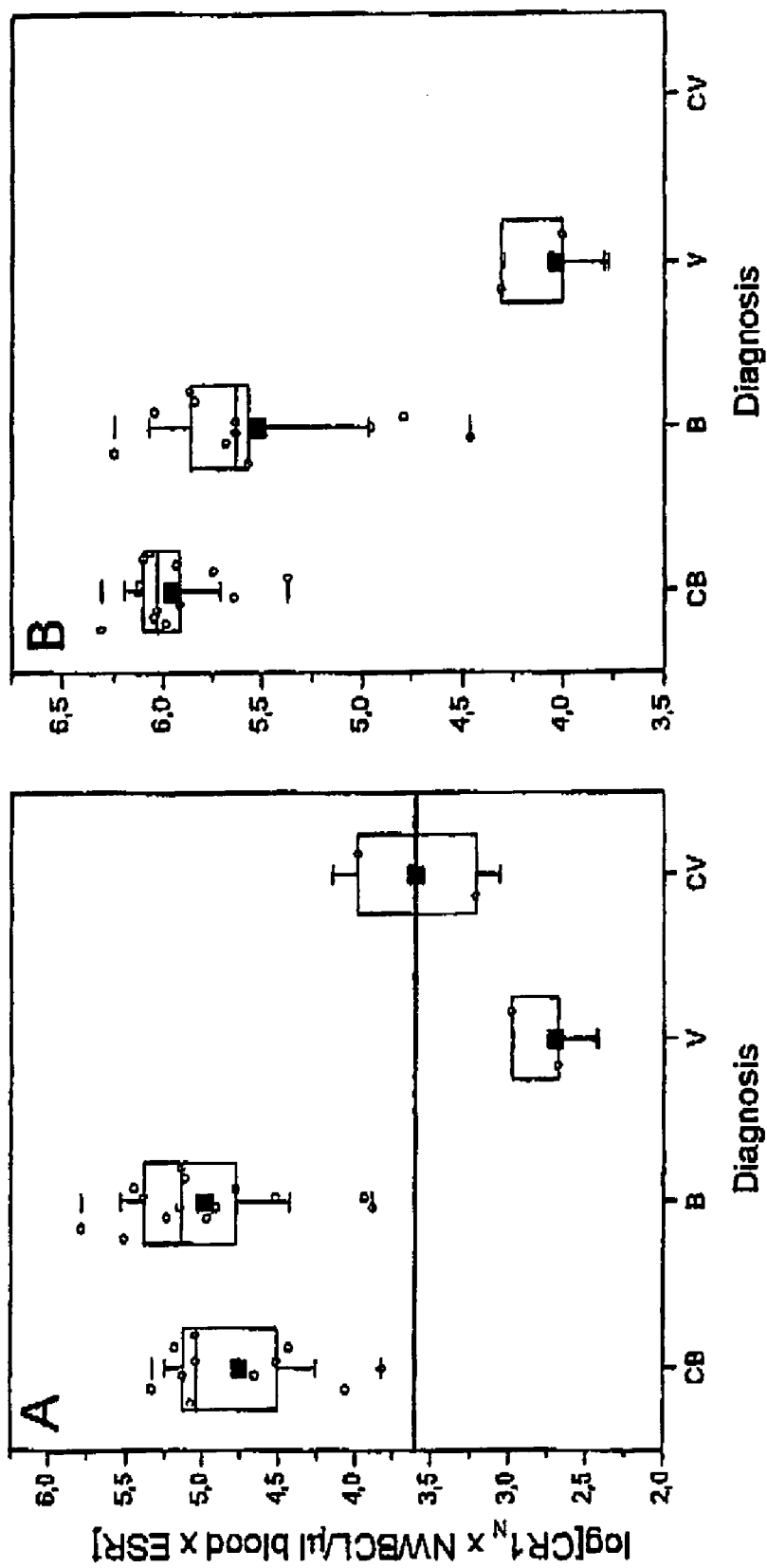
FIGS. 6A and 6B show the results obtained using Equation #2, CR1×NWBCL/µl blood×ESR, 6A: Experiment I, 6B: Experiment II. Patient groups as in FIG. 2.

Adding a term ESR into Equation #1 produces Equation #2, which can be written as CR1×NWBCL×ESR, wherein the NWBCL value is expressed per blood volume (µl). The ability of Equation #2 to separate bacterial infections from viral infections is almost equal with that of Equation #1 in Experiment I (FIG. 5A vs. FIG. 6A), but it particularly improves the resolution between bacterial and viral infections in Experiment II (FIG. 5B vs. FIG. 6B).

Equation #3

It is also possible to make sorting calculations without NWBCL measurements, by using the mean receptor expression values of neutrophils and monocytes (Equation #3). In viral infections, the mean expression of monocyte CR1 is higher than the expression of neutrophil CR1. The expression of monocyte FcγRI is higher and the expression of monocyte FcγRII lower in viral infections than in bacterial infections and controls.

$$\left(\frac{M}{N}\right)CR1 \times \left(\frac{F_{c\gamma}RI_M}{F_{c\gamma}RII_N}\right) \qquad \#3$$

It is possible to separate bacterial and viral infections in Experiments I and II with the help of Equation #3 (FIG. 7A and 7B). The product of Equation #3 in a viral infection is significantly higher compared with bacterial infections and controls (p<0.001) in Experiment I and also in Experiment II. Equation #3 is also a valuable tool for confirming an unclear result obtained using Equation #1 or #2.

REFERENCES

Isolauri, E., Pelto, L., Nuutila, J., Majamaa, Lilius, E. M., Salminen, S. (1997). Altered expression of IgG and complement receptors indicates a significant role of phagocytes in atopic dermatitis. J. Allergy Clin. Immunol 99, 707-713.

Leino, L., Sorvajarvi, K, Katajisto, J., Laine, M., Lilius, E. M., Pelliniemi, T. T., Rajamki, A., Silvoniemi, P, Nikoskelaien, J. (1997). Febrile infection changes the expression of IgG Fc receptors and complement receptors in human neutrophils in vivo. Clin. Exp. Immunol. 107, 37-43.

The invention claimed is:

1. A method for distinguishing a bacterial infection from a viral infection in a patient, comprising the steps of
   (a) measuring in a whole blood sample taken from said patient chemiluminescence of phagocytic cells in said whole blood sample induced by non-opsonized zymosan (NWBCL), expressed per blood volume,
   (b) separating in the blood sample erythrocytes from leukocytes by lysis,
   (c) determining in the leukocytes the expression of Complement Receptor 1 (CR1),
   (d) multiplying the value obtained at step (a) by the value obtained at step (c) using the equation CR1×NWBCL/µl whole blood,
   (e) comparing the value obtained from step (d) to the mean+/−the standard deviation (SD) of the average values obtained from samples having a confirmed viral or a confirmed bacterial infection wherein when:
      (i) the value from the patient is numerically higher than the mean+/−the SD value obtained from the samples having the confirmed viral infection, the patient is determined to have a bacterial infection,
      (ii) the value from the patient is numerically equal to the mean+/−the SD value obtained from the samples having a confirmed viral infection, the patient is determined to have a viral infection,
      (iii) the value from the patient is numerically lower than the mean+/−the SD value obtained from the samples having the confirmed bacterial infection, the patient is determined to have a viral infection, and
      (iv) the value from the patient is numerically equal to the mean+/−the SD value obtained from a sample having the confirmed bacterial infection, the patient is determined to have a bacterial infection.

2. The method according to claim 1, wherein the blood sample comprises heparin as an anticoagulant.

3. The method according to claim 1, wherein the zymosan used is sonicated zymosan.

4. The method according to claim 1, wherein the determinations from the blood samples are carried out within two hours, preferably within one hour from collecting the blood sample.

5. The method according to claim 1, comprising a further step of detecting the Erythrocyte Sedimentation Rate (ESR) value in a blood sample from the patient, and multiplying the value obtained at step (d) with said ESR value.

6. The method according to claim 5, wherein CR1×NWBCL/µl whole blood×ESR is used, wherein CR1 is the expression of Complement Receptor 1.

7. The method according to claim 1, wherein the CR1 expression is determined flow cytometrically.

8. The method according to claim 1, wherein the CR1 expression is determined luminometrically.

* * * * *